United States Patent [19]

Buckholtz et al.

[11] 4,024,198

[45] May 17, 1977

[54] PROCESS FOR THE CHLORINATION OF TOLUENE

[75] Inventors: Harry E. Buckholtz, Kenmore; Arun C. Bose, Tonawanda, both of N.Y.

[73] Assignee: Hooker Chemicals & Plastics Corporation, Niagara Falls, N.Y.

[22] Filed: Aug. 1, 1975

[21] Appl. No.: 601,692

[52] U.S. Cl. .................... 260/650 R; 252/429 R
[51] Int. Cl.$^2$ ................ C07C 25/06; C07C 25/08
[58] Field of Search ........................... 260/650 R

[56] References Cited
UNITED STATES PATENTS 1,741,305  12/1929  Jaeger ........................ 260/650 R
1,946,040  2/1934  Stoesser et al. ................ 260/650 R
3,226,447  12/1965  Bing et al. .................... 260/650 R Primary Examiner—D. Horwitz
Attorney, Agent, or Firm—Peter F. Casella; William J. Crossetta, Jr.; Arthur S. Cookfair

[57] ABSTRACT

In the process for the nuclear chlorination of alkylbenzenes, such as toluene, in the presence of a para-directing catalyst system comprising a substantially iron-free Lewis acid catalyst and thianthrene compound co-catalyst, wherein the reaction mixture is in contact with iron or an alloy thereof, the para-directing effect of the catalyst system is improved by the addition of an amide.

14 Claims, No Drawings

PROCESS FOR THE CHLORINATION OF TOLUENE

BACKGROUND OF THE INVENTION

The preparation of nuclear substituted chloro-compounds by reaction of chlorine with an alkylbenzene is well known. Thus, for example, the reaction of toluene with chlorine to form monochlorotoluene is well known and of considerable commercial importance. Such reactions are commonly carried out in the presence of a chlorination catalyst such as antimony chloride, ferric chloride, ferrous sulfide, aluminum chloride or the like in combination with sulfur monochloride. The usual products of such reactions are a mixture of various monochlorinated and/or polychlorinated compounds and various position isomers of these. For example, in the liquid phase substitution-chlorination of toluene, by reaction of chlorine and toluene, to form monochlorotoluene, the usual product is a mixture of orthochlorotoluene and parachlorotoluene which may, in addition, contain varying amounts of other chlorinated products such as dichlorotoluene, polychlorotoluenes and benzyl chlorides. Of the major reaction products, that is orthochlorotoluene and parachlorotoluene, the latter is the most commercially valuable. Based on the availability of two ortho- positions and one para-position, as chlorination sites a monochlorotoluene product having a ratio of orthochloro:-parachloro isomer of about 2:1 would be predicted. In the past, considerable effort has been expended in attempts to direct the chlorination reaction in such a manner as to lower the ratio of orthochlorotoluene to parachlorotoluene, that is, to discover reaction conditions under which the formation of parachlorotoluene is favored.

In co-pending application Ser. No. 601,219 (Case 3387), filed Aug. 1, 1975, the disclosure of which is hereby incorporated by reference, it is disclosed that a product having a substantially lower ratio of ortho-chloro:parachloro isomer is obtained when an alkylbenzene is reacted with chlorine in the presence of a catalyst system comprising a Lewis acid an a thianthrene compound.

On an industrial scale, chlorination reactions such as those discussed hereinabove are commonly carried out using equipment which is fabricated, at least in part, from iron or iron containing alloys. It has been found that under such conditions, utilizing a catalyst system comprising a Lewis acid and a thianthrene compound, the desired lowering of the ortho-para isomer ratio, although substantial, is considerably poorer than that achieved when non-iron-containing equipment is employed. It is believed that iron and/or steel equipment, dissolves slightly under the corrosive conditions present in chlorination reaction mixtures, to increase the concentration of iron to significantly higher levels than are present when the chlorination reactions are conducted in non-iron-containing equipment. Although the exact mechanism is not known, it is believed that the presence of excessive amounts of dissolved iron in the chlorination reaction mixture decreases the ability of such catalyst systems to specifically catalyze para-chlorination.

Accordingly, it is an object of this invention to provide an improved process for the para-directed chlorination of alkylbenzenes. It is a further object to provide a simple and effective method whereby the para-directed chlorination of alkylbenzenes, in the presence of a catalyst system comprising a Lewis acid and a thianthrene compound may be carried out in the presence of, or in contact with, iron-containing equipment or materials, without substantial deleterious effect on the enhanced para-directional activity of such catalyst system. It is a still further object of the present invention to provide an improved process for the commercial production of parachlorotoluene.

SUMMARY OF THE INVENTION

It has now been found that, in the process for the nuclear chlorination of alkylbenzenes, which comprises reacting, in the liquid phase, an alkylbenzene with chlorine, in the presence of a para-directing catalyst system comprising a substantially iron-free Lewis acid catalyst and a thianthrene compound co-catalyst, in the presence of iron-containing equipment, substantial improvement in the yield of parachloroalkylbenzenes is obtained when the chlorination reaction is carried out in the presence of an amide.

The exact mechanism whereby the presence of an amide results in an improvement in the para-direction of the chlorination reaction, is not fully understood. However, it may be theorized that under the conditions of the chlorination reaction, iron present in solution is converted to ferric chloride which is, of itself, an effective catalyst for the ring chlorination of aromatic compounds. Iron chlorides, however, while acting as effective chlorination catalysts, do not exert a strong directional effect and tend to catalyze the ring chlorination of alkyl aromatic compounds in such a manner that the ratio of orthochloro:parachloro products formed on chlorination closely approaches the 2:1 ratio which would be predicted in the absence of a para-directional effect. Thus, the presence of excessive amounts of iron chlorides in such a chlorination reaction mixture could, by exerting their own catalytic effect, minimize the enhanced para-directional effect which characterizes the action of thianthrene - Lewis acid catalyst systems. It is also possible that dissolved iron present in such chlorination reaction mixtures interferes with the specific para-directing capability of the catalyst system by chemically interacting with one or both components of the system to form a compound or complex which does not allow enhanced para-direction to occur.

Although the exact mechanism by which excessive iron interferes with the para-directing capability of the aforementioned catalyst systems in chlorination reactions is not known, it has been found, in accordance with the present invention, that the addition of an amide to such reaction mixtures allows the catalyst system to exert the desired enhancement of para-chlorination even in the presence of substantial amounts of dissolved iron. It is possible, though not certain, that amides exert this effect by virtue of their polar nature which allows them to form coordination complexes with dissolved iron, thus preventing it from either exerting a competitive catalytic effect or interfering with the normal para-directing catalytic effect of the catalyst system.

Various Lewis acid catalysts may be employed in the process of the present invention including, for example, compounds of antimony lead, molybdenum and aluminum, such as, the halides, oxyhalides, oxides, sulfides, sulfates, acids, or carbonates of these elements and mixtures of such compounds. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum carbonyl, lead sulfide, and the like. Although iron and iron compounds are known to function as Lewis acid catalysts, they provide no advantage in the process of the present invention. The addition of an amide serves to prevent the action of excessive and undesired amounts of iron and would, if an iron or iron type catalyst were employed, interfere with its catalytic action. Accordingly, iron or iron compounds are not contemplated as catalysts in accordance with the present invention. The preferred Lewis acid catalyst is antimony trichloride.

The thianthrene co-catalysts suitable for use in the process of this invention are thianthrene compounds or mixtures of thianthrene compounds characterized by the formula:

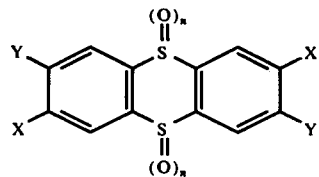

where $n$ is 0 to 1, X is an electron-withdrawing substituent, and Y is hydrogen or an electron-withdrawing substituent, and include, for example, thianthrene compounds, as well as the analogous sulfoxide compounds, wherein two or more electron-withdrawing substituents are present in the positions designated, as well as mixtures of such compounds. Suitable electron-withdrawing substituents which may be present on the thianthrene or sulfoxide nucleus in the $x$ and $y$ positions include for example, halo-, acetyl-, benzoyl- nitro-, sulfonyl-, cyano-, and quarternary amino-groups, and the like. The preferred thianthrene compounds are the halothianthrenes, especially the chlorothianthrenes. Particularly preferred is tetrachlorothianthrene, which may be employed as a co-catalyst in the process of the present invention, alone, or as a component of a mixture chlorothianthrenes.

Mixtures of chlorothianthrenes having as a major component thereof, tetrachlorothianthrene, may be prepared by the chlorination of thianthrene in monochlorotoluene in the presence of a Lewis acid catalyst. Details of the preparation of 2,3,7,8-tetrachlorothianthrene are disclosed in co-pending application Ser. No. 601,218 (Case 3513), filed August 1, 1975.

Chlorothianthrenes, such as di-, tri-, or tetra-chlorothianthrene including various position isomers thereof, may be employed as co-catalysts in the process of the present invention. Preferably, the isomers employed are those in which the chloro-substituent is present on one or more of the positions para to sulfur atoms. It has been found that the presence of a chloro or other electron-withdrawing substituent on the peri-positions, that is, positions adjacent to the sulfur atoms, tends to inhibit or lessen the para-directing effect of the thianthrene co-catalyst. Nevertheless, where mixtures of chlorothianthrenes are employed, compounds such as octachlorothianthrenes, heptachlorothianthrene, hexachlorothianthrene, pentachlorothianthrene, and others wherein a chlorine is present on one or more of the peri-positions, may be present in the mixture, preferably only as a minor component thereof. Similarly, when mixtures of other thianthrene compound co-catalysts of the present invention are employed, compounds having substituents in the peri-positions may be present, preferably only as a minor component of such mixture.

The amount of catalyst and co-catalyst employed may vary considerably. Thus, substantial benefits in terms of the lowering of the ratio of ortho- to para-isomer in the product may be achieved, for example when the catalyst system is present in amounts ranging from less than 0.01 percent to ten percent by weight or more of each based on the weight of alkylbenzene, and preferably in a molar ratio of catalyst:co-catalyst of about 0.1:1 to about 10:1. However, based on effectiveness as well as economic considerations, it is preferred to employ the catalyst and co-catylist in a total amount of about 0.05 to about 2.0 weight percent, based on the weight of the reaction mixture and in a molar ratio of catalyst:co-catalyst of about 0.25 to about 0.5.

Under atmospheric pressure, the chlorination reaction of the present invention may be carried out over a wide range of temperatures, ranging for example from sub-zero temperatures (Celsius scale) to over 100° C. For example, in the chlorination of toluene in the presence of a Lewis acid catalyst (SbCl$_3$) and thianthrene compound co-catalyst (a chlorothianthrene mixture) the chlorination was found to proceed readily at temperatures as low as −25° C to produce a monochlorotoluene product having a desirably low ortho:-para isomer ratio. (Below about −25° C, little or no reaction occurs.) The upper limit of temperatures is, of course, determined by the boiling point limitation, and may range as high as 150° C or higher. However, no practical advantage is gained through the use of higher temperatures and it is preferred to utilize temperatures in the range of about 0° C to about 125° C, and most preferably in the range of about 20° C to about 75° C. Although it is preferred to carry out the process at atmospheric pressures, subatmospheric or superatmospheric pressures may be employed if desired.

The preferred alkylbenzenes which may be chlorinated in accordance with the present invention include the various straight chain and branched chain alkylbenzenes as well as substituted alkylbenzenes. The preferred alkylbenzenes are those wherein the alkyl group is 1 to 4 carbon atoms, and most preferably toluene. In the chlorination of toluene in accordance with this invention, monochlorotoluene products having a ratio of orthochlorotoluene/parachlorotoluene of less than about 1.0 are obtainable. It will be appreciated that, although the preparation of monochloro alkylbenzenes, having a relatively high proportion of parachloro alkylbenzene, is an important object of the present invention, the monochloro-product may be further chlorinated, if desired, to produce higher chlorinated derivatives.

A wide variety of amides may be employed in the process of the present invention, the preferred amides being those characterized by the formula:

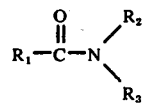

where $R_1$, $R_2$, and $R_3$ may be hydrogen, alkyl, or aryl groups. The preferred amides are those of the above formula wherein $R_1$, $R_2$ and $R_3$ are hydrogen or an alkyl of 1 to 12 carbon atoms. Typical amides which may be employed include for example, formamide, acetamide, propionamide, methylacetamide, ethylacetamide, N,N-dimethyl amide, N,N-diethyl amide, N,N-dipropyl amide, N,N-dimethyl caprylamide, N,N-dimethyl lauramide, N,N-dimethyl stearamide, N,N-dimethyl caproamide, and the like as well as mixtures of amides.

In accordance with a preferred mode of this invention, an alkyl aromatic compound to be chlorinated in the presence of a catalyst system comprising for example, $SbCl_3$ and a thianthrene compound is treated by the addition of an amide in an amount sufficient to allow any dissolved iron present in the reaction mixture, or which may be anticipated to dissolve therein during the reaction, to be rendered ineffective in interfering with the desired para-directing effect of the catalyst system. The amount of iron dissolved, for example from the reaction vessel, agitator, feed lines, or other equipment in contact with the reaction mixture, may vary considerably depending on the exact reaction conditions, such as temperature, to be employed, as well as the specific nature of the iron containing material employed. Any amount of amide added to the reaction mixture may be expected to provide a degree of improvement. However, maximum improvement may be obtained through the addition of an amount of amide based on the amount of dissolved iron anticipated. It may be expected, for example, that a greater amount of iron will be dissolved from a reaction vessel or iron than from a reaction vessel of stainless steel. The amount of iron which will be dissolved may be determined readily from analysis of dissolved iron in a reaction mixture after exposure, under reaction conditions, to the reaction equipment. Although the exact amount is not critical, it is preferred to add the amide in an amount of about 0.01 to about 10 parts by weight of amide per part of dissolved iron, and most preferably about 0.1 to about 3.0 parts by weight of amide per part of dissolved iron. Although the amount of amide employed may vary depending on the nature of iron containing equipment as well as the reaction conditions, the amide is typically employed in amounts ranging from about 0.0001 to about 1.0 percent by weight of amide, based on the weight of alkylbenzene.

The following specific examples are provided to further illustrate this invention. It is to be understood, however, that the specific details of the examples are presented for purposes of illustration and are not to be construed as a limitation on the invention. In the examples, the detrimental interfering effect of dissolved iron with the para-directional effect of the catalyst system and the ability of amides to overcome this detrimental effect is demonstrated. In Example 1, a toluene chlorination was carried out with the aid of a Lewis acid-thianthrene compound catalyst system, in all glass equipment. The ratio of orthochlorotoluene:parachlorotoluene in the reaction product was 0.82. In Example 2 an identical experiment was carried out except that the glass agitator previously used was replaced with an AISI 1010 steel agitator. The agitator was weighed before and after the reaction and the weight loss noted. The ratio of orthochlorotoluene:parachlorotoluene in the reaction product increased substantially to 1.19. In Examples 3 and 4, the procedure of Example 2 was duplicated except that an amide was added to the reaction mixture prior to chlorination. In the latter examples the ratio of orthochlorotoluene:parachlorotoluene in the reaction product was 0.82. In the examples, unless otherwise indicated, all parts and percentages are by weight and all temperatures are in degrees Celsius.

EXAMPLE 1

A mixture of 877 parts of toluene, 0.897 parts of 2,3,7,8-tetrachlorothianthrene, and 0.573 parts of antimony trichloride was charged to an all glass reaction vessel equipped with a glass agitator and glass condenser. The reaction mixture was heated to about 60° C and maintained at about that temperature, with agitation, while 580 parts of chlorine was slowly introduced into the mixture. Upon completion of the reaction, the reaction mixture was purged with nitrogen to remove hydrogen chloride and excess chlorine. Analysis of the reaction mixture by gas chromatographic methods established it to have an orthochlorotoluene:parachlorotoluene ratio of 0.82.

EXAMPLE 2

The procedure of Example 1 was repeated except that the glass agitator was replaced by an AISI 1010 steel agitator. The agitator was weighed before and after and found to have lost 0.009 parts. Gas chromatographic analysis of the reaction product established it to have an orthochlorotoluene'parachlorotoluene ratio of 1.19.

EXAMPLE 3

The procedure of Example 2 was repeated except that 0.58 parts of formamide was added to the reaction mixture prior to the introduction of chlorine. Weight loss of the steel agitator during the reaction, was 0.051 parts. Analysis of the reaction product established it to have an orthochlorotoluene:parachlorotoluene ratio of 0.82.

EXAMPLE 4

The procedure of Example 4 was repeated except that prior to chlorination there was added to the reaction mixture about 0.12 parts of a mixture of about 90 percent of N,N-dimethyl caproamide and 10 percent of N,N-dimethyl caprylamide. Weight loss of the steel agitator during the reaction was 0.011 parts. Analysis of the reaction product established it to have an orthochlorotoluene:parachlorotoluene ratio of 0.82.

What is claimed is:

1. In the process for the nuclear chlorination of alkylbenzenes which comprises reacting in the liquid phase, and alkylbenzene with chlorine, at a temperature from below about −25° to above about 150° Celsius in the presence of about 0.01 to about 10.0 percent by weight of a para-directing catalyst system comprising a substantially iron-free Lewis acid catalyst and a thianthrene co-catalyst characterized by the formula:

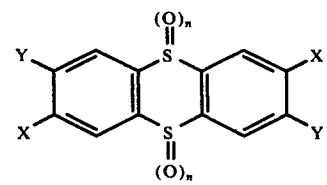

wherein $n$ is 0 to 1, $x$ is an electron-withdrawing substituent and Y is hydrogen or an electron-withdrawing substituent, in the presence of iron or an ally thereof the improvement which comprises carrying out said process in the presence of an amide characterized by the formula:

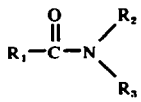

where $R_1$, $R_2$, and $R_3$ are independently selected from the group consisting of hydrogen and alkyl groups of 1–12 carbon atoms.

2. A process according to claim 1 wherein the alkylbenzene is characterized by an alkyl group of 1 to 4 carbon atoms.

3. A process according to claim 2 wherein the Lewis acid catalyst is antimony trichloride and the thianthrene co-catalyst comprises chlorothianthrene.

4. A process according to claim 2 wherein the alkylbenzene is toluene.

5. A process according to claim 4 wherein the Lewis acid catalyst is antimony trichloride.

6. A process according to claim 5 wherein the thianthrene co-catalyst comprises 2,3,7,8-tetrachlorothianthrene.

7. A process according to claim 6 wherein the amide is formamide.

8. A process according to claim 6 wherein $R_1$, $R_2$, and $R_3$ are alkyl groups of 1 to 12 carbon atoms.

9. A process according to claim 8 wherein the amide is a mixture of N,N-dimethyl caproamide and N,N-dimethyl caprylamide.

10. In the process for the nuclear chlorination of toluene which comprises reacting toluene with chlorine at temperature of about 20° to about 75° Celsius, in the presence of about 0.01 to about 10.0 percent by weight, based on the weight of toluene, of a catalyst system comprising antimony trichloride catalyst and a chlorothianthrene co-catalyst having as the major component thereof, 2,3,7,8-tetrachlorothianthrene, in molar ratio of catalyst:co-catalyst of about 0.25 to about 0.5, in the presence of iron or an alloy thereof, the improvement which comprises carrying out said process in the presence of about 0.0001 to about 1.0 weight percent, based on the weight of toluene, of an amide, characterized by the formula:

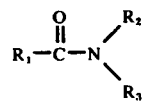

wherein $R_1$, $R_2$, and $R_3$ are independently selected from the group consisting of hydrogen and alkyl groups of 1 to 12 carbon atoms.

11. A process according to claim 10 wherein the amide is formamide.

12. A process according to claim 10 wherein the amide is a mixture of about 90 percent by weight of N,N-dimethyl caproamide and about 10 percent by weight of N,N-dimethyl caprylamide.

13. The process of claim 1 wherein said Lewis acid catalyst is at least one selected from the group of aluminum chloride, antimony trichloride, antimony pentachloride, antimony trioxide, antimony tetraoxide, antimony pentaoxide, antimony trifluoride, antimony oxychloride, molybdenum carbonyl and lead sulfide.

14. In the proces for the nuclear chlorination of alkybenzenes which comprises reacting in the liquid phase, an alkylbenzene with chlorine, at a temperature from below about −25° to above about 150° Celsius in the presence of about 0.01 to about 10.0 percent by weight of a para-directing catalyst system comprising a substantially iron-free Lewis acid catalyst and a thianthrene co-catalyst characterized by the formula:

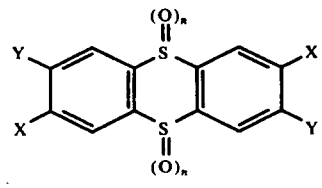

wherein $n$ is 0 to 1, $x$ is an electron-withdrawing substituent and Y is hydrogen or an electron-withdrawing substituent, in the presence of iron or an alloy thereof, the improvement which comprises carrying out said process in the presence of an amide selected from the group of formamide, acetamide, propionamide, methylacetamide, ethlacetamide, N,N-dimethyl amide, N,N-diethylamide, N,N-dipropyl amide, N,N-dimethyl caprylamide, N,N-dimethyl lauramide, N,N-dimethyl stearamide, N,N-dimethyl caproamide, and mixtures thereof.

* * * * *